(12) United States Patent
Choi et al.

(10) Patent No.: US 7,954,397 B2
(45) Date of Patent: Jun. 7, 2011

(54) SURGICAL SLAVE ROBOT

(75) Inventors: Seung Wook Choi, Seongnam-si (KR); Jong Seok Won, Yongin-si (KR)

(73) Assignee: meerecompany, Hwaseong-si (KR)

( * ) Notice: Subject to any disclaimer, the term of this patent is extended or adjusted under 35 U.S.C. 154(b) by 0 days.

(21) Appl. No.: 12/676,852

(22) PCT Filed: Jul. 23, 2009

(86) PCT No.: PCT/KR2009/004092
§ 371 (c)(1),
(2), (4) Date: Mar. 5, 2010

(87) PCT Pub. No.: WO2010/044536
PCT Pub. Date: Apr. 22, 2010

(65) Prior Publication Data
US 2010/0224022 A1    Sep. 9, 2010

(30) Foreign Application Priority Data
Oct. 13, 2008    (KR) .................. 10-2008-0100181

(51) Int. Cl.
*B25J 18/00*    (2006.01)
(52) U.S. Cl. ........................ 74/490.01; 901/15
(58) Field of Classification Search ............... 74/490.01, 74/490.05, 490.06; 901/15, 16, 27, 28, 29; 606/130; 414/744.2, 744.3, 744.4, 744.5
See application file for complete search history.

(56) References Cited

U.S. PATENT DOCUMENTS

| | | | |
|---|---|---|---|
| 5,078,140 A * | 1/1992 | Kwoh | 600/417 |
| 6,441,577 B2 * | 8/2002 | Blumenkranz et al. | 318/568.11 |
| 2005/0096502 A1 * | 5/2005 | Khalili | 600/106 |

FOREIGN PATENT DOCUMENTS

| | | |
|---|---|---|
| EP | 1815949 A1 | 8/2007 |
| KR | 10-695471 B1 | 3/2007 |
| WO | WO 97/29690 A1 | 8/1997 |
| WO | WO 2007/045810 A2 | 4/2007 |

* cited by examiner

*Primary Examiner* — Richard W Ridley
*Assistant Examiner* — Phillip A Johnson
(74) *Attorney, Agent, or Firm* — Birch, Stewart, Kolasch & Birch, LLP

(57) ABSTRACT

A surgical slave robot is disclosed. The surgical slave robot, for performing a surgical operation with a surgical instrument installed on an end portion of a robot arm, can include: a main body; a major support arm that is coupled to the main body such that the major support arm is movable along one direction; a minor support arm rotatably coupled to the major support arm; and a plurality of the robot arms rotatably coupled to the minor support arm. By coupling a twofold support arm of a major and minor support arm to a tower-shaped main body and coupling multiple robot arms to the support arms, the surgical slave robot may be constructed with a compact and slim size that occupies a small amount of space, making it possible to position the surgical robot close to the patient while providing space for the surgeon to access the patient.

7 Claims, 5 Drawing Sheets

SURGICAL SLAVE ROBOT

CROSS-REFERENCE TO RELATED APPLICATIONS

This application claims foreign priority benefits under 35 U.S.C. sctn. 119(a)-(d) to PCT/KR2009/004092, filed Jul. 23, 2009, which is hereby incorporated by reference in its entirety.

BACKGROUND

1. Technical Field

The present invention relates to a surgical slave robot.

2. Description of the Related Art

In the field of medicine, surgery refers to a procedure in which a medical device is used to make a cut or an incision in or otherwise manipulate a patient's skin, mucosa, or other tissue, to treat a pathological condition. A surgical procedure such as a laparotomy, etc., in which the skin is cut open and an internal organ, etc., is treated, reconstructed, or excised, may entail problems of blood loss, side effects, pain, and scars, and as such, the use of robots is currently regarded as a popular alternative.

A conventional set of surgical robots may include a master robot, which is manipulated by the doctor to generate and transmit the necessary signals, and a slave robot, which receives the signals from the master robot to actually apply the manipulation to the patient. Typically, the slave robot may be mounted in the operating room, and the master robot may be mounted in a manipulation room, with the master robot and slave robot connected by a wired and/or wireless system to allow remote operation of a surgical procedure.

Here, the slave robot may be faced with the conflicting requirements of having to be positioned close to the patient undergoing surgery, while not occupying an excessive amount of space so that anesthetists, clinical staff, and nurses may approach the patient.

To satisfy these requirements, conventional slave robots have been mounted in a variety of ways, such as by positioning the slave robot near the patient, attaching the slave robot to the surgical bed, and installing the slave robot on the ceiling of the operating room and lowering the slave robot to the position of the patient as necessary. Each of these approaches has its advantages and disadvantages, and it is difficult to say which one approach is superior.

The information in the background art described above was obtained by the inventors for the purpose of developing the present invention or was obtained during the process of developing the present invention. As such, it is to be appreciated that this information did not necessarily belong to the public domain before the patent filing date of the present invention.

SUMMARY

An aspect of the present invention is to provide a slave robot that offers the strength, stability, functionality, and precision required for robot surgery, is small and slim in size, so that the surgeon may readily access the patient, and also provides greater freedom in pre-surgery preparations for both the patient and the robot.

One aspect of the present invention provides a surgical slave robot for performing a surgical operation with a surgical instrument installed on an end portion of a robot arm, where the surgical slave robot includes: a main body; a major support arm that is coupled to the main body such that the major support arm is movable along one direction; a minor support arm rotatably coupled to the major support arm; and a plurality of the robot arms rotatably coupled to the minor support arm.

The main body can be formed as a tower-shaped column mounted on a floor of an operating room in correspondence to a position of an operating table. Also, the main body can be supported by a wheel such that the main body is movable within an operating room, in which case a stopper can be coupled to the main body adjacent to the wheel such that an action of the stopper may secure the main body at a particular position.

The major support arm can be coupled to the main body by a sliding system such that the major support arm is movable upward and downward along the main body, and the minor support arm can be coupled to an end portion of the major support arm by a SCARA system. Also, the major support arm can be tiltably coupled to the main body, and the minor support arm can be tiltably coupled to the major support arm.

The main body can be formed with a size capable of housing the major support arm, and the major support arm can be coupled to the main body by a sliding system such that the major support arm is movable along a retracting and protracting direction in relation to the main body.

The robot arm can include two or more link members axially coupled to each other, where the lines extending from coupling axes between the link members can meet at a particular point on an end portion of the instrument.

Additional aspects, features, and advantages, other than those described above, will be obvious from the claims and written description below.

In a preferred embodiment of the present invention, a twofold support arm of a major and minor support arm may be coupled to a tower-shaped main body, and multiple robot arms may be coupled to the support arms, so that a surgical slave robot may be constructed with a compact and slim size that occupies a small amount of space, making it possible to position the surgical robot close to the patient while providing space for the surgeon to access the patient.

Also, while maintaining the strength, stability, functionality, and precision required for robot surgery, the overall size and mass of the robot may be reduced, so that the entire robot may easily be separated from the patient in case of an emergency. Furthermore, by coupling a multiple number of robot arms to the support arm, all of the robot arms can be folded at once instead of folding each of the robot arms, so that pre-surgery preparations for the robot can be performed more freely.

DETAILED DESCRIPTION

Figure 1:
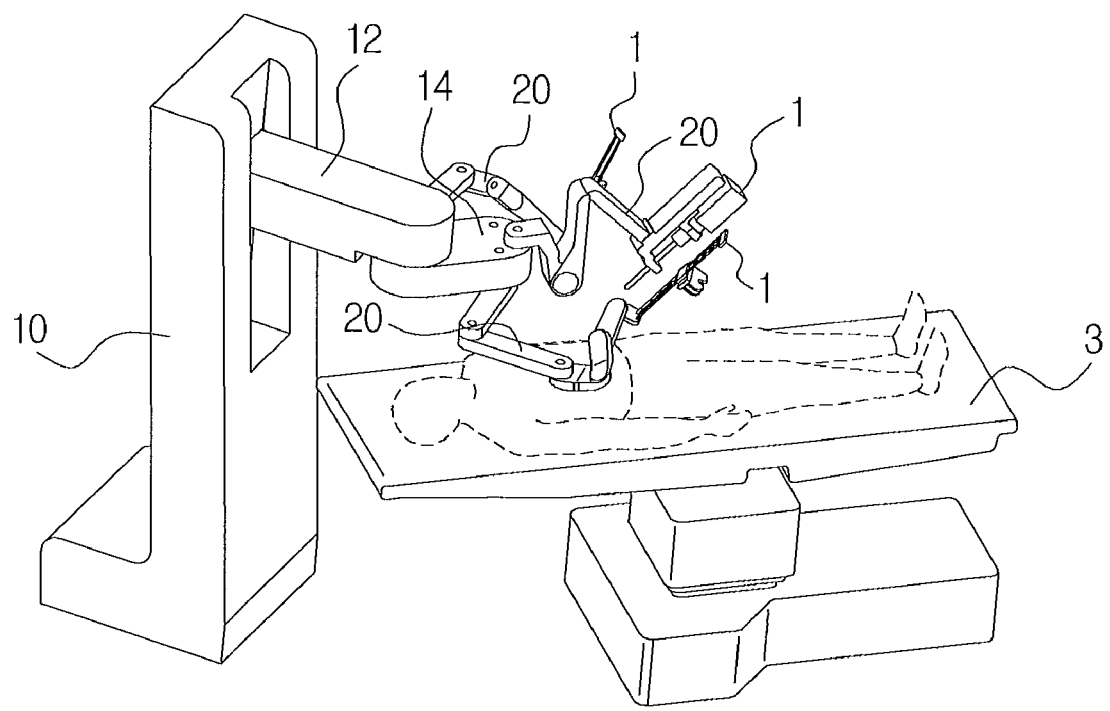
FIG. 1 is a perspective view of a surgical slave robot according to a preferred embodiment of the present invention.

As the present invention allows for various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention. In the written description, certain detailed explanations of related art are omitted when it is deemed that they may unnecessarily obscure the essence of the present invention.

While such terms as "first" and "second," etc., may be used to describe various components, such components must not be limited to the above terms. The above terms are used only to distinguish one component from another.

The terms used in the present specification are merely used to describe particular embodiments, and are not intended to limit the present invention. An expression used in the singular encompasses the expression of the plural, unless it has a clearly different meaning in the context. In the present specification, it is to be understood that the terms "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Certain embodiments of the present invention will be described below in detail with reference to the accompanying drawings. Those components that are the same or are in correspondence are rendered the same reference numeral regardless of the figure number, and redundant descriptions are omitted.

Figure 2:
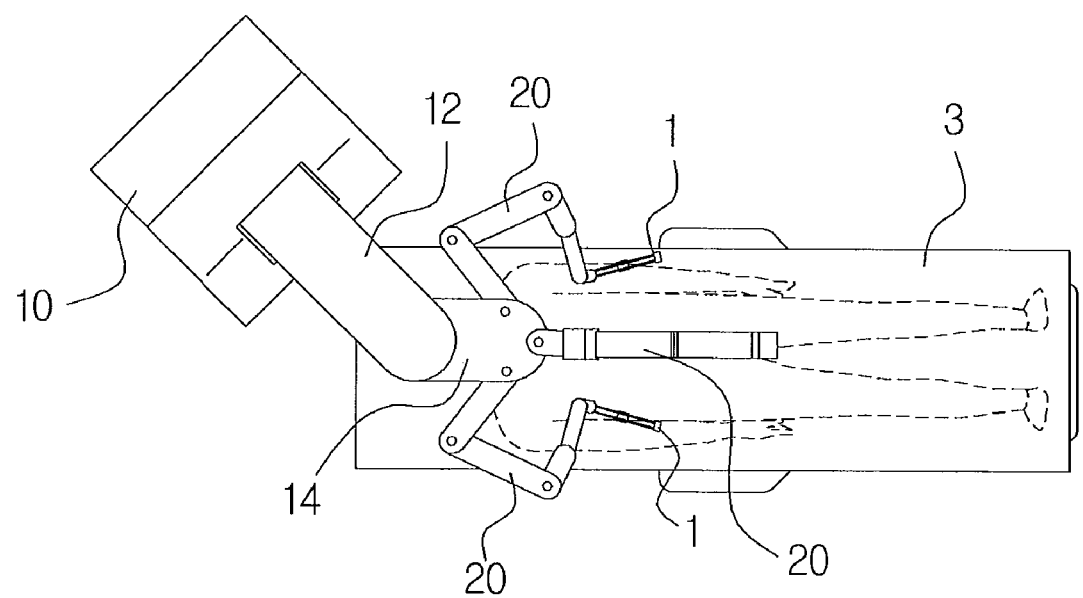
FIG. 2 is a plan view of a surgical slave robot according to a preferred embodiment of the present invention.
Figure 3:
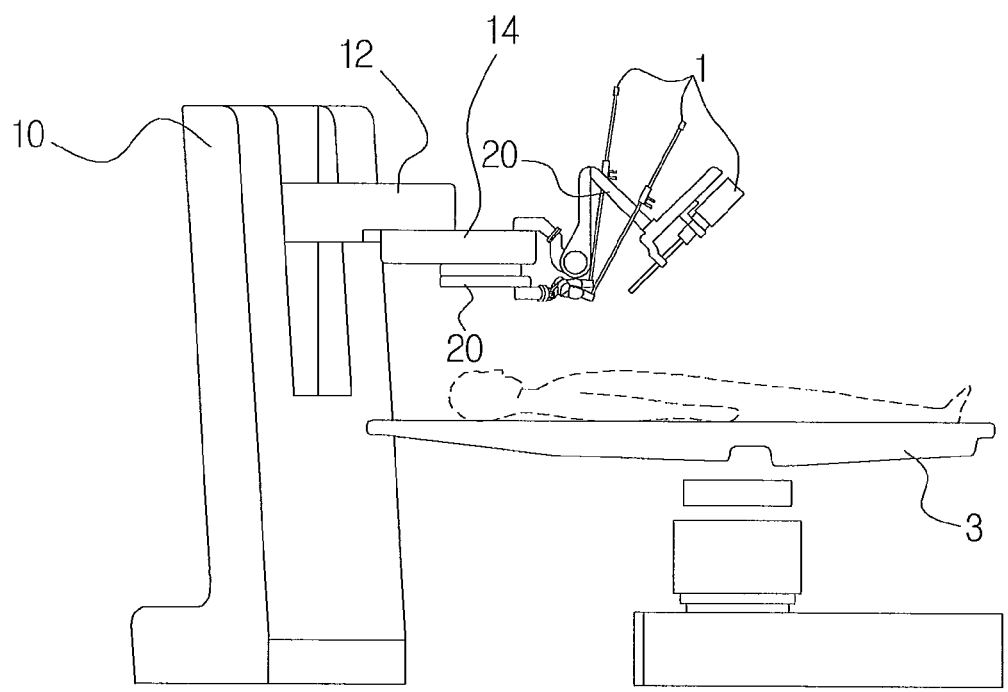
FIG. 3 is a side-elevational view of a surgical slave robot according to a preferred embodiment of the present invention.
Figure 4:
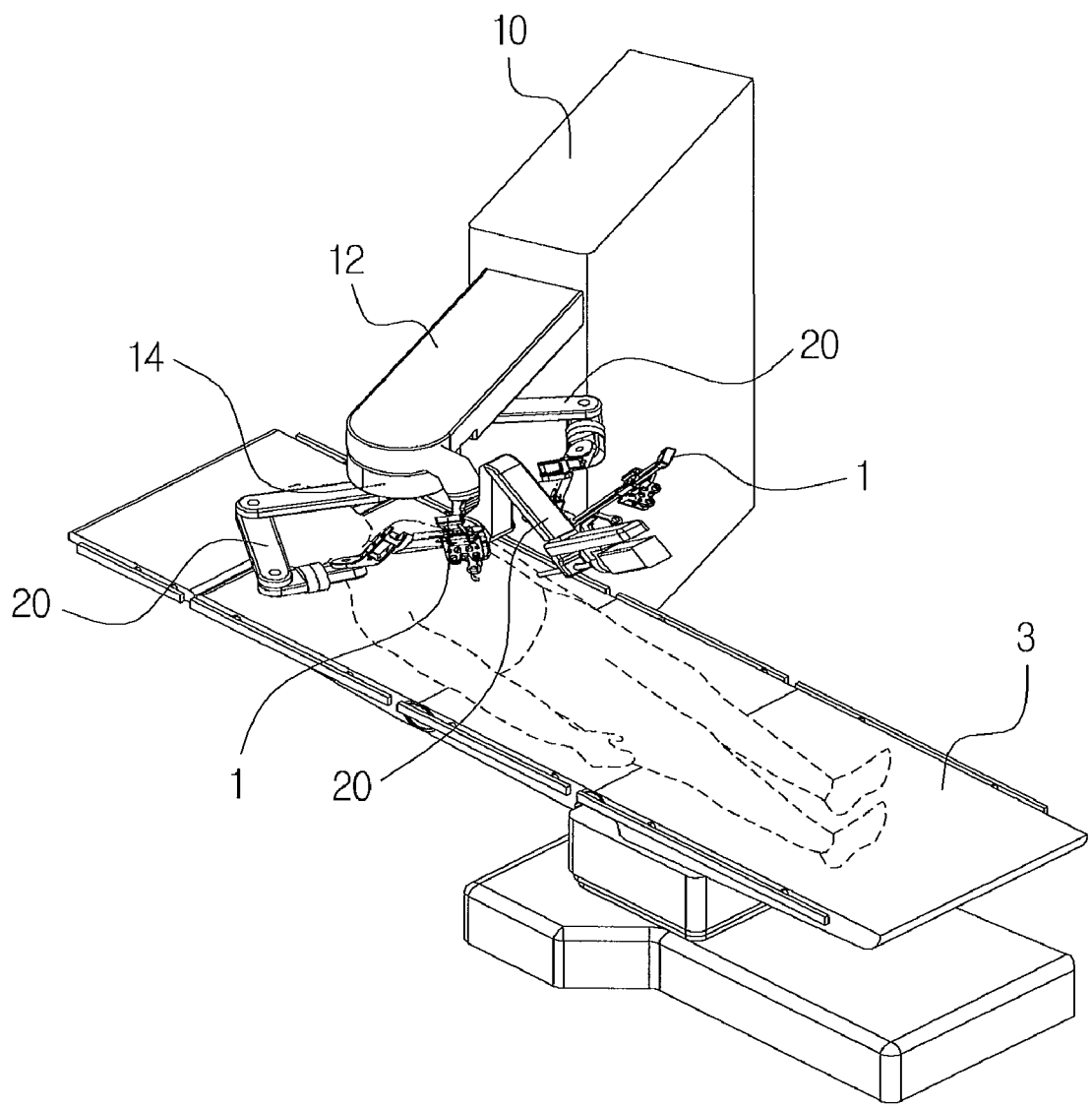
FIG. 4 is a perspective view of a surgical slave robot according to another preferred embodiment of the present invention.

FIG. 1 is a perspective view of a surgical slave robot according to a preferred embodiment of the present invention, FIG. 2 is a plan view of a surgical slave robot according to a preferred embodiment of the present invention, FIG. 3 is a side-elevational view of a surgical slave robot according to a preferred embodiment of the present invention, and FIG. 4 is a perspective view of a surgical slave robot according to another preferred embodiment of the present invention. Illustrated in FIG. 1 through FIG. 4 are instruments 1, an operating table 3, a main body 10, a major support arm 12, a minor support arm 14, and robot arms 20.

One feature of this embodiment is that, in constructing a surgical slave robot, a twofold support arm, i.e. a major support arm 12 and a minor support arm 14, may be sequentially coupled to a tower-shaped main body, and multiple robot arms 20 may be coupled to an end portion of the minor support arm 14, so that the robot may be constructed to be compact and slim overall.

The surgical slave robot may have to satisfy conflicting requirements. That is, the surgical slave robot may have to be positioned close to the patient when activated, while enabling clinical staff, etc., to access the patient without obstruction, and the surgical slave robot may have to be positioned over the body of the patient when activated, while guaranteeing sterilization to eliminate the risk of infection for the patient.

Moreover, the surgical slave robot may have to provide the levels of strength, accuracy, and dexterity sufficient for activation, while providing a small, slim size and light weight, and the surgical slave robot may have to be mounted in a stable manner, while being capable of moving freely and occupying a small area. Furthermore, the surgical slave robot may have to provide freedom in pre-surgery preparations for both the patient and the robot.

Various mounting types have been conceived to best satisfy each of these conflicting requirements, including the ceiling mount type, table mount type, floor mount type, and patient mount type. The following table compares the advantages and disadvantages of each type.

| Type | Advantages | Disadvantages |
| --- | --- | --- |
| Ceiling Mount | Good accessibility to patient | Requires exclusive operating room Mounting position limited Risk of interference from lighting |
| Table Mount | Convenience when adjusting operating table (if necessary) | Inability to withstand high loads Insufficient stability Requires manual attachment |
| Floor Mount | Ability to withstand high loads Good mobility during surgery | Low accessibility to patient |
| Patient Mount | Follows movement of patient | Robot weight limited Low attachment stability Low accessibility |

From a general observation of the above, it can be concluded that an ideal set of properties for a surgical slave robot is to allow good accessibility to the patient like the ceiling mount type, and to allow good mobility and provide a small size and a slim form to occupy a small area of the operating room while providing sufficient levels of strength, accuracy, and dexterity, like the floor mount type.

This embodiment is to provide an ideal set of properties for a surgical slave robot such as that described above. Instead of a conventional slave robot structure, in which each of the robot arms 20 are coupled to the main body so that the robot is large in volume, low in mobility, and complicated in activation, the present embodiment may include support arms 12, 14 coupled to the main body, and multiple robot arms 20 installed on the support arms 12, 14, to implement a slave robot structure that is slim and easy to move and activate.

That is, instead of having the multiple robot arms 20 coupled directly to the main body 10, a surgical slave robot according to the present embodiment may include a twofold support arm 12, 14 protruding from the main body 10 and multiple robot arms 20 coupled to an end portion of the support arm.

The twofold support arm 12, 14 may be composed of the major support arm 12, which is coupled to the main body 10, and the minor support arm 14, which is coupled to an end portion of the major support arm 12, where the two support arms 12, 14 may be operated to move a robot arm 20 to a position required for surgery.

For the purpose of operating the support arms 12, 14, the support arms 12, 14 can be coupled to the main body 10 by way of a variety of coupling systems, such as a sliding system, SCARA system, etc. FIGS. 1 to 3 illustrate an example in which the major support arm 12 is coupled to the main body 10 by way of a slide movement system, and in which the minor support arm 14 is coupled to the major support arm 12 by way of a SCARA (Selective Compliance Assembly Robot Arm) system.

The SCARA system is widely used in the industry due to its simple structure and high performance to cost ratio. The SCARA system provides a fast operating speed and is generally used in assembling and packaging work or work involving picking up and moving things.

Thus, by coupling the major support arm 12 to the main body 10 such that the major support arm 12 is able to move in one direction, and coupling the minor support arm 14 to the major support arm 12 such that the minor support arm 14 is able to rotate, the robot arms 20 can be made to move to a required position.

The multiple number of robot arms 20 may be rotatably coupled to an end portion of the minor support arm 14, so that a robot arm 20 that has been moved by the operation of the major/minor support arms 12, 14 may be activated by a surgeon to perform robot surgery. As described above, the operation of the support arms 12, 14 and the actions of the robot arms 20 during a robot surgery procedure can be implemented by manipulating the master robot.

Various instruments 1 required for surgery, such as a laparoscope, skin holder, suction line, effector, etc., can be installed on the end portions of the robot arms 20 for performing the surgical operation.

In this way, by manufacturing the robot arms 20 in small sizes and concentrating the robot arms on the end portion of the support arm, instead of mounting the robot arms 20 directly on the main body 10, the surgical slave robot according to this embodiment can be manufactured in a much more compact form compared to existing robot structures, and may thus occupy a smaller amount of space and provide reduced size and mass. Also, in comparison to the table mounting type, the entire slave robot can be separated from the patient more easily in the case of an emergency.

In order to protect the surgery patient from secondary infection, a process known as "draping" may be performed on a surgical slave robot that entails covering the robot arms 20 with sanitized vinyl, etc. Whereas for a conventional robot, each of the robot arms 20 may have to be draped individually, for a slave robot according to the present embodiment, all of the robot arms 20 can be draped simultaneously by just covering the support arm, so that pre-surgery preparations can be performed easily and quickly.

The descriptions below will be provided, with reference to FIGS. 1 to 3, for an example in which the major support arm 12 is coupled by a sliding system and the minor support arm 14 is coupled by a SCARA system. As described above, however, this method of coupling the support arms 12, 14 is only an example, and it is obvious that various robot operating systems can be employed for moving the robot arms 20 to a desired position. For instance, the major support arm 12 can be coupled to the main body 10 by way of a sliding system or a SCARA system, and the minor support arm 14 can also be coupled to the major support arm 12 by way of a sliding system or a SCARA system.

As illustrated in FIGS. 1 to 3, a slave robot according to the present embodiment may have the main body 10 mounted at a particular distance from the operating table 3, and may have the two support arms 12, 14 extending from the main body 10 to the operating table 3, with the robot arms 20 for performing the actions necessary for surgery coupled to the end portion.

The main body 10 of the robot may be mounted in the form of a tower-shaped column on the floor of the operating room in correspondence to the position of the operating table 3, and the major support arm 12 and the minor support arm 14 may be coupled extending from the main body 10 towards the operating table 3. At the end portion of the minor support arm 14, a multiple number of robot arms 20 for performing the surgery may be installed, so that the robot surgery procedure may be performed directly above the patient.

In cases where the main body 10 is manufactured in the form of a tower-shaped column, the main body 10 does not necessarily have to be mounted on the operating room floor, and may include wheels (not shown) installed on the bottom surface by which the main body 10 may be moved to a desired position within the operating room. In cases where wheels are installed on the main body 10 in this manner, a robot according to the present embodiment can be constructed to be moved manually by a user. The robot can also be constructed such that the wheels move automatically according to user input.

If wheels are installed on the main body 10 as described above, the robot can be secured at a particular position as necessary, and for this purpose, a stopper (not shown) can be mounted on the main body 10 adjacent to a wheel to secure the main body 10 at a desired position.

The stopper can be formed as a brake that restricts the rotation of the wheel to secure the main body 10. The stopper can also be formed as a support that is installed near the wheel and protracted to secure the main body 10, in a manner similar to that of an outrigger used in a mobile crane.

By installing the robot arms 20 on the main body 10 with the support arms 12, 14 interposed in-between, the robot's main body 10 itself can be mounted at a position separated from the operating table 3, while the robot arms 20 can be manipulated at a very close position to the patient, satisfying all of the conflicting requirements for the slave robot described above.

As the support arms 12, 14 may serve to extend the robot arms 20 from the robot's main body to the position of the patient, the major support arm 12 and minor support arm 14 may be rotatably coupled to the main body 10, allowing the robot arms 20 to move to a point in 3-dimensional space according to the manipulation of the surgeon.

FIGS. 1 and 3 illustrate an example in which the major support arm 12 is coupled to the main body 10 by a sliding system. That is, the major support arm 12 may slide up and down along the main body 10 and move the components coupled to the major support arm 12, i.e. the minor support arm 14 and the robot arms 20, to a particular height (along the z-axis) in 3-dimensional space.

The minor support arm 14 may be coupled to the major support arm 12 by a SCARA system to enable the robot arms 20 coupled to the minor support arm 14 to freely move along a plane (the x-y plane) at a particular height.

As a result, the robot arms 20 may be moved to a particular position in 3-dimensional space, such as the surgical site of the patient, for example, according to the operation of the major support arm 12 and the minor support arm 14, and the surgeon may manipulate the master robot to activate the robot arms 20 and thus perform robot surgery. In this way, a slave robot according to the present embodiment can be manufactured in a compact form while maintaining the strength, accuracy, and dexterity required for surgery.

Although FIGS. 1 to 3 illustrate an example in which the major support arm 12 is coupled to the main body 10 by a sliding system and the minor support arm 14 is coupled to the major support arm 12 by a SCARA system, the present invention is not limited to this mode of coupling, and it is obvious that various robot operating systems can be applied.

In cases where the main body 10 is formed with a size capable of housing the major support arm 12, that is, in cases where the width (or depth) of the main body 10 is as long as the length of the major support arm 12 as in FIG. 4, the major support arm 12 can be coupled to the main body 10 such that the major support arm 12 is able to slide along its lengthwise direction. Then, the major support arm 12 can be retracted when not used and protracted from the main body 10 when needed, to be used for robot surgery.

By slidably coupling the major support arm 12 in this way to be retractable in and protractible from the main body 10, the slave robot can be made much slimmer. Since the robot can be protracted to a sufficient length when needed for robot surgery, and the robot arms 20 can readily be made to reach the surgical site, the level of dexterity required for surgery can be maintained.

Also, the major support arm 12 according to the present embodiment can be tiltably coupled to the main body 10, and in addition, the minor support arm 14 can also be tiltably coupled to major support arm 12. That is, the major support arm 12 and/or minor support arm 14 can be axially coupled to the main body 10 or major support arm 12, or a hinge can be interposed in a middle portion of the major support arm 12 and/or minor support arm 14, so that the major support arm 12 and/or minor support arm 14 may rotate about the coupling axis or hinge (not shown) to provide a tilting action.

In cases where the support arms 12, 14 are thus implemented to provide tilting actions, the robot arms 20 coupled to the end portion of the support arms 12, 14 can be made to move a considerable amount of distance merely by slightly rotating the support arms 12, 14, whereby the robot arms 20 can easily be moved to a desired position.

Figure 5:
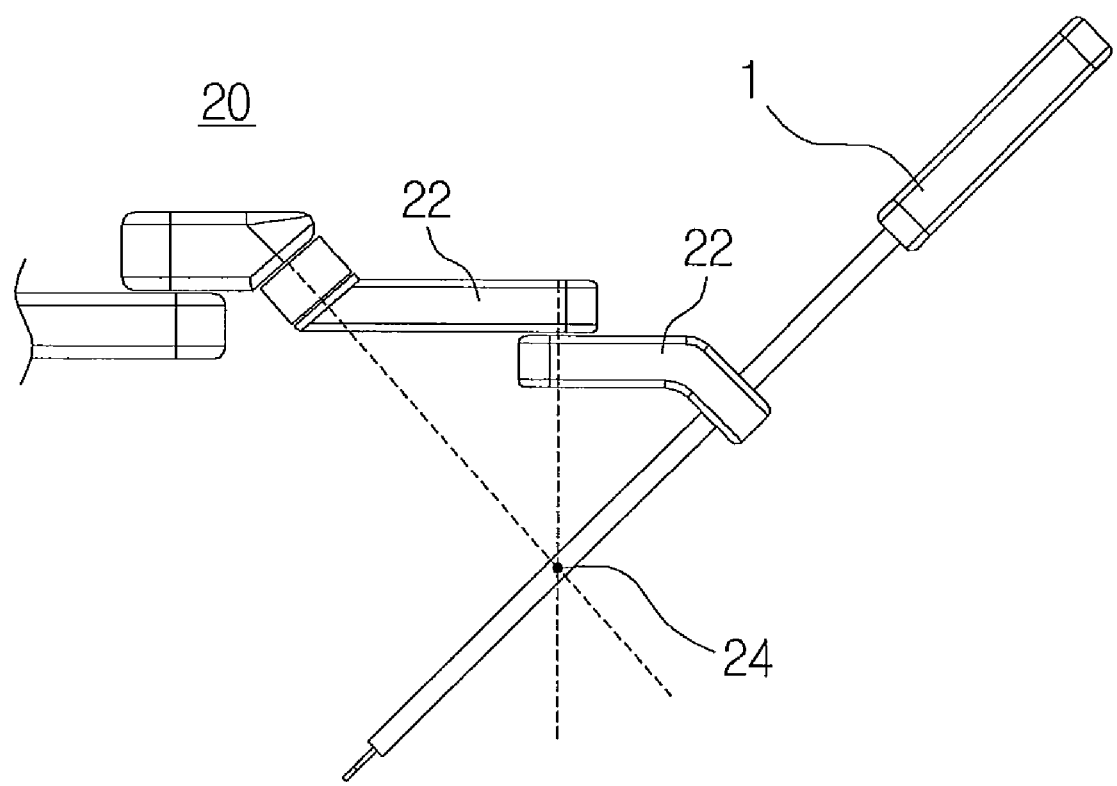
FIG. 5 is a schematic drawing of a robot arm according to a preferred embodiment of the present invention.

FIG. 5 is a schematic drawing of a robot arm according to a preferred embodiment of the present invention. Illustrated in FIG. 5 are instruments 1, robot arms 20, link members 22, and an RCM point 24.

In this embodiment, the robot arms 20 may be coupled to an end portion of the minor support arm 14, where each of the link members 22 of the robot arms 20 may be coupled in a way that implements an RCM (remote center of motion) function, so that the robot arms 20 may readily perform a surgical procedure at a particular part of the patient.

That is, in performing a surgical procedure with an instrument 1 installed on a front end of a robot arms 20, a composition in which the instrument 1 moves in accordance with the movement of the robot arm 20 can create a risk of unnecessary damage to the patient's skin. To resolve this problem, an imaginary center point of rotation can be preset on a particular position on the end portion of the instrument 1, and the robot arm 20 can be controlled such that the instrument 1 rotates about this point, where this imaginary center point may be referred to as a "remote center of motion" or "RCM."

As illustrated in FIG. 5, a robot arm 20 can include a multiple number of axially coupled link members 22. By adjusting the shapes of the link members 22 and/or the directions of the coupling axes such that the lines extending from the coupling axes of the link members 22 meet at the RCM point 24, an RCM function can be implemented for the rotation of the robot arm 20.

While the present invention has been described with reference to particular embodiments, it is to be appreciated that various changes and modifications can be made by those skilled in the art without departing from the spirit and scope of the present invention as defined by the appended claims.

What is claimed is:

1. A surgical slave robot for performing a surgical operation with a surgical instrument installed on an end portion of a robot arm, the surgical slave robot comprising:
   a main body;
   a major support arm movably coupled to the main body, the major support arm movable along one direction;
   a minor support arm rotatably coupled to the major support arm, the minor support arm having an upper surface and a lower surface; and
   a plurality of the robot arms rotatably coupled to at least one of the upper and lower surfaces of the minor support arm.

2. The surgical slave robot of claim 1, wherein the main body is formed as a tower-shaped column configured to be mounted on a floor of an operating room in correspondence to a position of an operating table.

3. The surgical slave robot of claim 1, wherein the minor support arm is coupled to an end portion of the major support arm by a SCARA system.

4. The surgical slave robot of claim 1, wherein the minor support arm is tiltably coupled to the major support arm.

5. The surgical slave robot of claim 1, wherein the robot arm comprises two or more link members axially coupled to each other, and
   lines extending from coupling axes between the link members meet at a particular point on an end portion of the instrument.

6. The surgical slave robot of claim 1, wherein the robot arm comprises at least first and second link members connected to one another by a pivotable connection, each link member having a top surface and a bottom surface, the top surface of a first link member contacting the bottom surface of a second link member at the pivotable connection.

7. The surgical slave robot of claim 1, wherein the robot arms are connected to the top and bottom surface of the minor support arm.

* * * * *